(12) United States Patent
Sugawara et al.

(10) Patent No.: US 11,483,126 B2
(45) Date of Patent: Oct. 25, 2022

(54) PHYSIOLOGICAL INFORMATION SYSTEM, PHYSIOLOGICAL INFORMATION SENSOR AND PHYSIOLOGICAL INFORMATION PROCESSING APPARATUS

(71) Applicant: NIHON KOHDEN CORPORATION, Tokyo (JP)

(72) Inventors: Hironori Sugawara, Tokorozawa (JP); Yukio Koyama, Tokorozawa (JP); Hiroshi Kubo, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 236 days.

(21) Appl. No.: 16/658,710

(22) Filed: Oct. 21, 2019

(65) Prior Publication Data

US 2020/0145183 A1 May 7, 2020

(30) Foreign Application Priority Data

Nov. 2, 2018 (JP) .............................. JP2018-207532

(51) Int. Cl.
*H04L 7/04* (2006.01)
*G16H 40/67* (2018.01)
(Continued)

(52) U.S. Cl.
CPC .................. *H04L 7/04* (2013.01); *A61B 5/72* (2013.01); *G16H 40/67* (2018.01); *H04L 67/12* (2013.01)

(58) Field of Classification Search
CPC ........... H04L 7/04; H04L 67/12; G16H 40/67; A61B 5/0002; A61B 5/72; A61B 5/0015; A61B 5/0026
See application file for complete search history.

(56) References Cited

U.S. PATENT DOCUMENTS 6,697,372 B1 * 2/2004 McAlear ................. H04L 12/46
370/402
8,711,023 B2 * 4/2014 Guido .................... F02D 35/027
341/155
(Continued)

FOREIGN PATENT DOCUMENTS

JP 2003018585 A * 1/2003 ................ H04J 3/04
JP 2004-040185 A 2/2004
(Continued)

OTHER PUBLICATIONS

Japanese Office Action dated Aug. 9, 2022 issued in Japanese Patent Application No. 2018-207532.

*Primary Examiner* — Franklin D Balseca
(74) *Attorney, Agent, or Firm* — Pearne & Gordon LLP (57) ABSTRACT

A physiological information system includes: a plurality of physiological information sensors configured to acquire physiological information data of a subject being tested, and a physiological information processing apparatus communicatively connected to each of the plurality of physiological information sensors. The physiological information processing apparatus is configured to transmit a synchronous packet toward each of the plurality of physiological information sensors. Each of the plurality of physiological information sensors is configured to: acquire the physiological information data of the subject being tested; receive the synchronous packet transmitted from the physiological information processing apparatus or a trigger signal associated with the synchronous packet; start AD conversion processing for the acquired physiological information data when receiving the synchronous packet or the trigger signal; and transmit the physiological information data converted into digital data to the physiological information processing apparatus.

15 Claims, 6 Drawing Sheets

(51) Int. Cl.
*H04L 67/12* (2022.01)
*A61B 5/00* (2006.01)

(56) References Cited

U.S. PATENT DOCUMENTS

| | | |
|---|---|---|
| 9,497,017 B1 | 11/2016 | Kim et al. |
| 10,320,407 B1* | 6/2019 | Kamath ................ H03M 1/145 |
| 2003/0175025 A1 | 9/2003 | Watanabe et al. |
| 2004/0088445 A1 | 5/2004 | Weigold et al. |
| 2005/0125709 A1* | 6/2005 | McKim ................ G06F 11/273 |
| | | 714/25 |
| 2006/0064522 A1 | 3/2006 | Weigold et al. |
| 2007/0285531 A1 | 12/2007 | Watanabe et al. |
| 2013/0191562 A1 | 7/2013 | Foster et al. |
| 2015/0178964 A1 | 6/2015 | Mato et al. |
| 2017/0300653 A1* | 10/2017 | Hresko ................ G16H 40/60 |

FOREIGN PATENT DOCUMENTS

| | | |
|---|---|---|
| JP | 2008-183082 A | 8/2008 |
| JP | 2010-259650 A | 11/2010 |
| JP | 2012-034840 A | 2/2012 |
| JP | 2013-254510 A | 12/2013 |
| JP | 2015-119741 A | 7/2015 |

\* cited by examiner

PHYSIOLOGICAL INFORMATION SYSTEM, PHYSIOLOGICAL INFORMATION SENSOR AND PHYSIOLOGICAL INFORMATION PROCESSING APPARATUS

CROSS-REFERENCE TO RELATED APPLICATIONS

This application is based on and claims priority under 35 USC 119 from Japanese Patent Application No. 2018-207532 filed on Nov. 2, 2018, the contents of which are incorporated herein by reference.

TECHNICAL FIELD

The present disclosure relates to a physiological information system, a physiological information sensor and a physiological information processing apparatus.

BACKGROUND ART

JP-A-2015-119741 discloses a system including a physiological information sensor and a physiological information display device communicatively connected to the physiological information sensor. In the system disclosed in JP-A-2015-119741, a vital information sign acquired by the physiological information sensor is transmitted to the physiological information display device, as an analog signal. Then, the transmitted vital information sign is converted into a digital signal by an AD (Analog-to-Digital) converter of the physiological information display device, and the vital information sign is subjected to digital signal processing (DSP).

When communicatively connecting a plurality of physiological information sensors to a physiological information processing apparatus (for example, a patient monitor), there are considerable needs for unifying communication interfaces for interconnecting the physiological information processing apparatus and the respective physiological information sensors. Also, there are considerable needs for securing a degree of layout freedom of each physiological information sensor as the number of the physiological information sensors to be mounted to a subject being tested increases. In this respect, it is considered to interconnect the physiological information processing apparatus and each physiological information sensor by using a communication interface (for example, a USB interface) for transmitting digital data.

However, in a case in which each physiological information sensor transmits physiological information data to the physiological information processing apparatus, as digital data, since a timing at which AD conversion processing (particularly, sampling processing) for the physiological information data (analog data) starts and a transmission start timing of the physiological information data are different in the respective physiological information sensors, there is a concern that the physiological information processing apparatus cannot execute predetermined processing for each physiological information data (digital data) temporally synchronized with each other. Therefore, there is room for improvement on usability of the physiological information system configured by the plurality of physiological information sensors and the physiological information processing apparatus.

An object of the presently disclosed subject matter is to provide a physiological information system, a physiological information sensor and a physiological information processing apparatus that have improved usability.

SUMMARY OF INVENTION

A physiological information system related to a first aspect of the present disclosure includes: a plurality of physiological information sensors configured to acquire physiological information data of a subject being tested, and a physiological information processing apparatus communicatively connected to each of the plurality of physiological information sensors. The physiological information processing apparatus is configured to transmit a synchronous packet toward each of the plurality of physiological information sensors. Each of the plurality of physiological information sensors is configured to: acquire the physiological information data of the subject being tested; receive the synchronous packet transmitted from the physiological information processing apparatus or a trigger signal associated with the synchronous packet; start AD conversion processing for the acquired physiological information data when receiving the synchronous packet or the trigger signal; and transmit the physiological information data converted into digital data to the physiological information processing apparatus.

A physiological information sensor related to a second aspect of the present disclosure is a sensor communicatively connected to a physiological information processing apparatus and configured to acquire physiological information data of a subject being tested. The physiological information sensor is configured to: acquire the physiological information data of the subject being tested; receive a synchronous packet transmitted from the physiological information processing apparatus or a trigger signal associated with the synchronous packet; start AD conversion processing for the acquired physiological information data when receiving the synchronous packet or the trigger signal; and transmit the physiological information data converted into digital data to the physiological information processing apparatus.

A physiological information processing apparatus related to a third aspect of the present disclosure is an apparatus communicatively connected to a plurality of physiological information sensors configured to acquire physiological information data of a subject being tested. The physiological information processing apparatus is configured to: transmit a synchronous packet to the plurality of physiological information sensors; receive physiological information data, which has been converted into digital data through AD conversion processing, from each of the plurality of physiological information sensors; and execute predetermined processing for the received physiological information data. The AD conversion processing is started when the synchronous packet transmitted from the physiological information processing apparatus or a trigger signal associated with the synchronous packet is received.

A physiological information system related to a fourth aspect of the present disclosure includes: a plurality of physiological information sensors configured to acquire physiological information data of a subject being tested; and a physiological information processing apparatus communicatively connected to each of the plurality of physiological information sensors. The physiological information processing apparatus is configured to transmit a synchronous packet toward each of the plurality of physiological information sensors. Each of the plurality of physiological information sensors is configured to: acquire the physiological information data of the subject being tested; receive the synchronous packet transmitted from the physiological information processing apparatus or a trigger signal associated with the synchronous packet; start predetermined processing when receiving the synchronous packet or the trigger signal; and transmit the physiological information data converted into digital data to the physiological information processing apparatus.

According to the presently disclosed subject matter, it is possible to provide the physiological information system, the physiological information sensor and the physiological information processing apparatus that have improved usability.

DETAILED DESCRIPTION OF EMBODIMENTS

Figure 1:
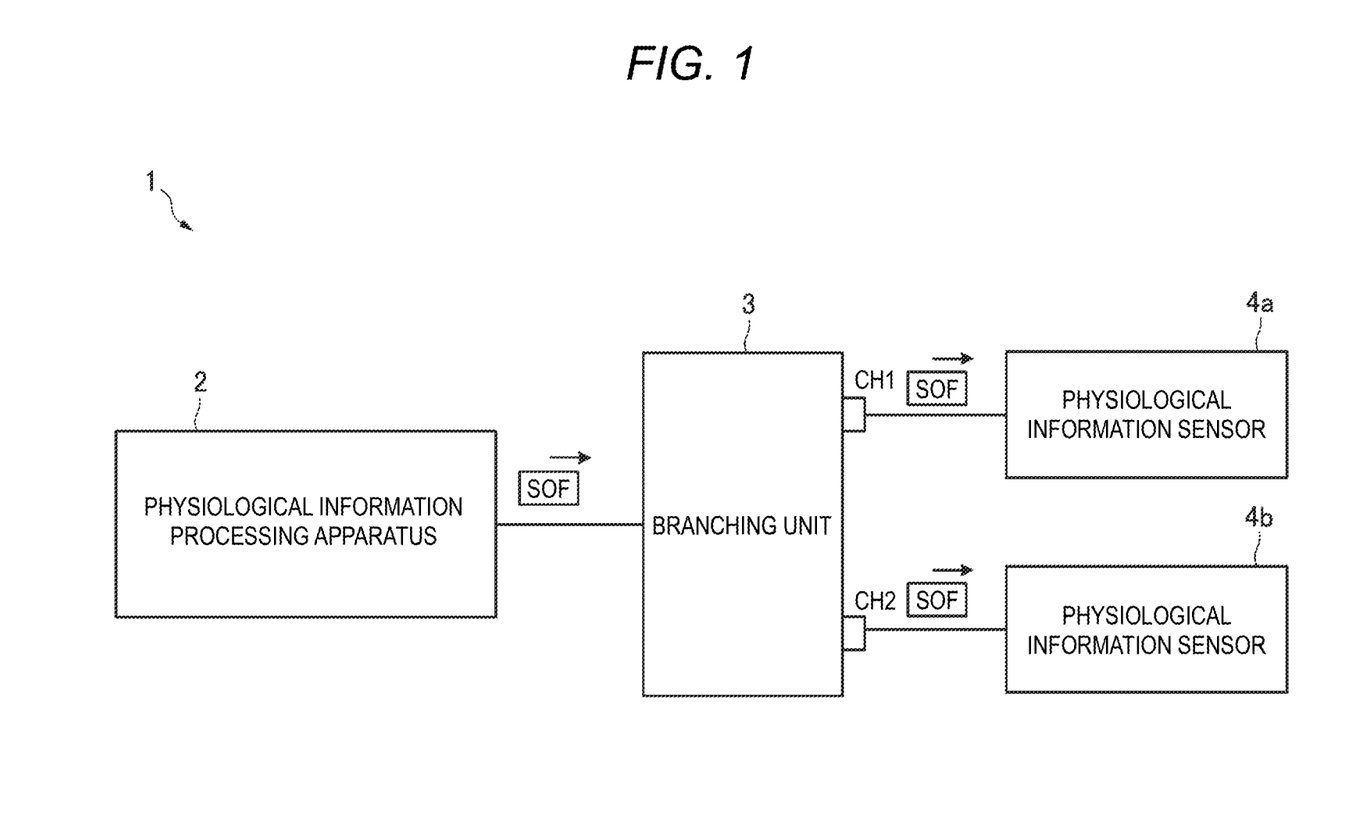
FIG. 1 illustrates an example of an entire configuration of a physiological information system in accordance with an exemplary embodiment of the presently disclosed subject matter (hereinafter, referred to as the exemplary embodiment)

Hereinafter, an exemplary embodiment will be described with reference to the drawings. First, an entire configuration of a physiological information system 1 in accordance with an exemplary embodiment of the presently disclosed subject matter (hereinafter, referred to as the exemplary embodiment) is described. FIG. 1 illustrates an example of the entire configuration of the physiological information system 1.

As illustrated in FIG. 1, the physiological information system 1 can include a physiological information processing apparatus 2 (hereinafter, simply referred to as 'processing device 2'), a branching unit 3, and physiological information sensors 4a and 4b. As described later, the processing device 2 has a USB (Universal Serial Bus) interface, and is communicatively connected to the branching unit 3 via a USB cable. The branching unit 3 can include a USB hub having a plurality of connection ports, and one or more processors such as a CPU (Central Processing Unit).

The physiological information sensor 4a can include a USB interface and is communicatively connected to the branching unit 3 via a USB cable. In particular, the physiological information sensor 4a is connected to a connection port CH1 of the branching unit 3 (USB hub) via a USB cable (an example of a digital communication cable). Same or similarly, the physiological information sensor 4b can include a USB interface and is communicatively connected to the branching unit 3 via a USB cable. In particular, the physiological information sensor 4b is connected to a connection port CH2 of the branching unit 3 (USB hub). In this way, the processing device 2 is communicatively connected to the physiological information sensors 4a and 4b via the USB cables, via the branching unit 3. Meanwhile, in the exemplary embodiment, for convenience of descriptions, the physiological information system 1 includes the two physiological information sensors. However, the number of the physiological information sensors is not particularly limited. For example, the physiological information system 1 can include three or more physiological information sensors. Also, the number of the branching unit 3 is not particularly limited, and the physiological information system 1 can include two or more branching units 3. In this case, the plurality of branching units 3 can be connected in a cascade manner.

Figure 2:
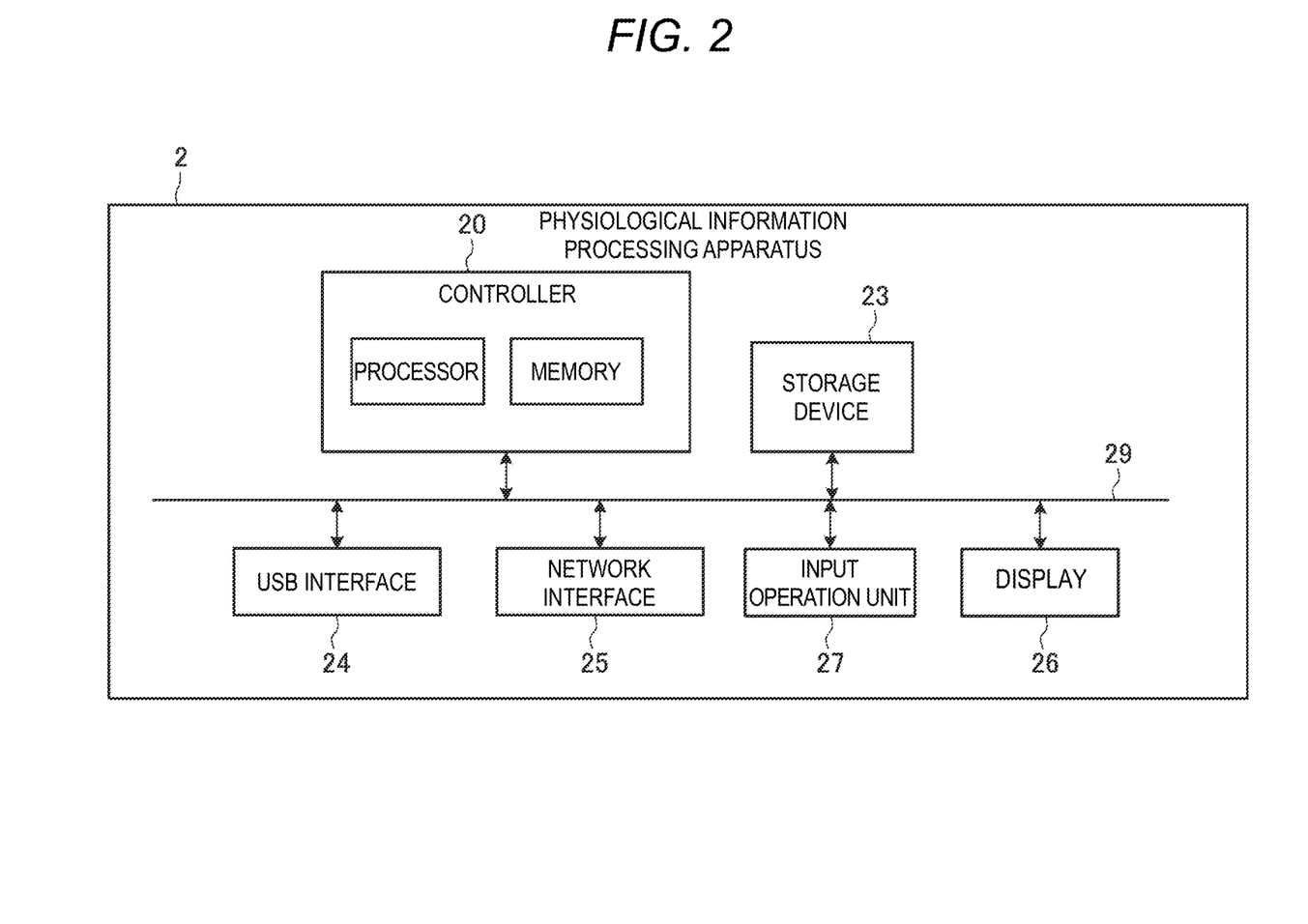
FIG. 2 illustrates an example of a configuration of a physiological information processing apparatus in accordance with the exemplary embodiment.

Subsequently, a configuration of the processing device 2 is described with reference to FIG. 2. FIG. 2 illustrates an example of the configuration of the processing device 2. As illustrated in FIG. 2, the processing device 2 can include a controller 20, a storage device 23, a USB interface 24, a network interface 25, a display 26, and an input operation unit 27. The constitutional elements are connected in communication with each other via a bus 29.

The processing device 2 may be a medical device (a patient monitor, and the like) configured to display trend graphs of a plurality of physiological information data of a subject being tested, and may be, for example, a personal computer, a workstation, a smart phone, a tablet, a wearable device (for example, a smart watch, an AR glass, and the like) to be mounted on a body (for example, an arm, a head, and the like) of a healthcare professional, and the like.

The controller 20 is configured to control operations of the processing device 2, and can include one or more memories and one or more processors. The one or more memories are configured to store a computer-readable command (program). For example, the one or more memories can be configured by a ROM (Read Only Memory) in which diverse programs and the like are stored, a RAM (Random Access Memory) having a plurality of work areas in which diverse programs and the like to be executed by the one or more processors are stored. Also, the one or more memories can be configured by one or more flash memory, and the like. The one or more processors may be, for example, a CPU, am MPU (Micro Processing Unit) and/or a GPU (Graphics Processing Unit). The CPU may be configured by a plurality of CPU cores. The GPU may be configured by a plurality of GPU cores. The one or more processors may be configured to develop a program, which is designated from the diverse programs incorporated in the storage device 23 or the ROM, on the RAM, and to execute a variety of processing in cooperation with the RAM.

The storage device 23 may be, for example, a storage device (storage) such as an HDD (Hard Disk Drive), an SSD (Solid State Drive), a flash memory and the like, and is configured to store programs and diverse data. In the storage device 23, the physiological information data of the subject being tested transmitted from the physiological information sensors 4a and 4b may be stored. For example, the transmitted physiological information data may be stored in the storage device 23 via the USB interface 24.

The network interface 25 is configured to connect the processing device 2 to a communication network. Specifically, the network interface 25 can include a variety of wired connection terminals for performing communication with an external apparatus such as a server via the communication network. Also, the network interface 25 can include a variety of processing circuits, an antenna and the like for performing wireless communication with an access point. A wireless communication standard between the access point and the processing device 2 may be, for example, Wi-Fi (registered trademark), Bluetooth (registered trademark), ZigBee (registered trademark), LPWA or fifth-generation mobile communication system (5G). The communication network may be, LAN (Local Area Network), WAN (Wide Area Network), Internet or the like.

The display 26 may be a display device such as a liquid crystal monitor, an organic electroluminescence display, and the like, or may be a transmission type or non-transmission type head mount display to be mounted to an operator's head. Also, the display 26 may be a projector device configured to project an image on a screen.

The input operation unit 27 is configured to receive an input operation of the healthcare professional who operates the processing device 2, and to generate an instruction signal in accordance with the input operation. The input operation unit 27 may be, for example, a touch panel superimposed on the display 26, operation buttons attached on a housing, a mouse and/or a keyboard. After the instruction signal generated by the input operation unit 27 is transmitted to the controller 20 via the bus 29, the controller 20 executes a predetermined operation, in accordance with the instruction signal.

The USB interface 24 is an interface of a USB standard for communicatively connecting the processing device 2 to peripheral devices such as the physiological information sensors 4a and 4b, the branching unit 3 and the like. The USB interface 24 can include a connection terminal to which a connector of the USB cable is to be input.

Figure 3:
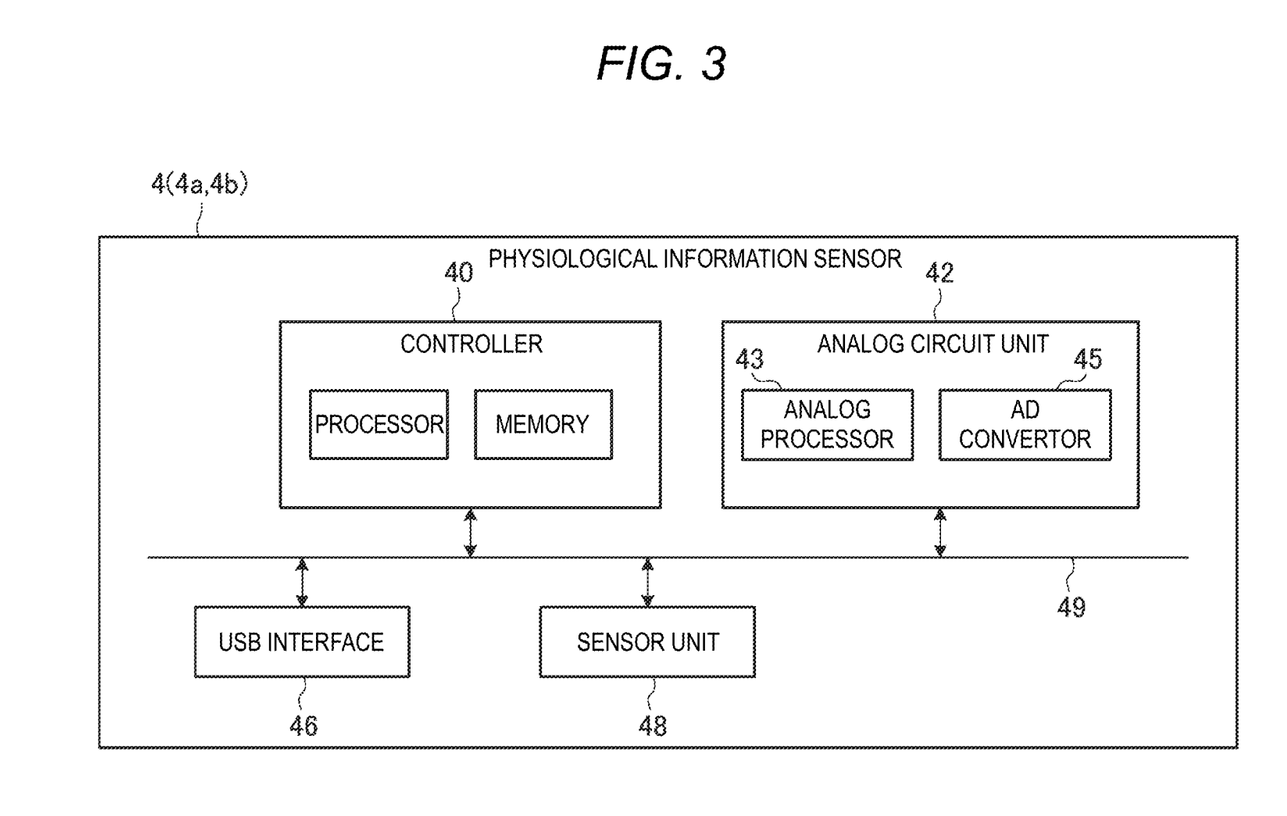
FIG. 3 illustrates an example of a configuration of a physiological information sensor in accordance with the exemplary embodiment.

Subsequently, a configuration of the physiological information sensors 4a and 4b is described with reference to FIG. 3. FIG. 3 illustrates an example of the configuration of the physiological information sensors 4a and 4b. Meanwhile, in descriptions below, the physiological information sensors may be collectively referred to as 'physiological information sensor 4'. As illustrated in FIG. 3, the physiological information sensor 4 can include a controller 40, an analog circuit unit 42, a USB interface 46, and a sensor unit 48. The constitutional elements are connected in communication with each other via a bus 49.

The controller 40 is configured to control operations of the physiological information sensor 4, and can include one or more memories and one or more processors. The one or more memories can include a ROM and a RAM. The one or more processors may be, for example, a CPU, a GPU and/or an MPU. The USB interface 46 is an interface for communicatively connecting the physiological information sensor 4 to the peripheral devices such as the processing device 2, the branching unit 3 or the like. The USB interface 46 can include a connection terminal to which a connector of the USB cable is to be input. The sensor unit 48 is configured to acquire the physiological information data of the subject being tested, as analog data. In a case in which the physiological information sensor is an ECG (electrocardiogram) sensor, the sensor unit 48 is configured to acquire ECG data (an example of the physiological information data) of the subject being tested. Also, in a case in which the physiological information sensor is a pulse sensor, the sensor unit 48 is configured to acquire pulse data (an example of the physiological information data) of the subject being tested. In this case, the sensor unit 48 can include a light emitter configured to emit red light and/or infrared light toward a physiological tissue such as a finger of the subject being tested, and a light detector configured to detect the red light and/or infrared light emitted from the light emitter and penetrating the physiological tissue of the subject being tested or reflected therefrom. The sensor unit 48 can be mounted a part of the body of the subject being tested. Meanwhile, in the exemplary embodiment, the type of the physiological information sensor 4 is not particularly limited, and the physiological information sensor 4 may be, an ECG sensor, a pulse sensor, a blood pressure sensor, a body temperature sensor, a respiration sensor, or the like. For example, in a case in which the physiological information sensor 4a is the ECG sensor, the physiological information sensor 4b may be a physiological information sensor (for example, the pulse sensor) different from the ECG sensor.

The analog circuit unit 42 can include an analog processor 43, and an AD convertor 45. The analog processor 43 is configured to execute predetermined processing for the physiological information data (analog data) acquired by the sensor unit 48. For example, the analog processor 43 is configured to amplify the physiological information data and to filter a noise component (for example, a high-frequency component) of the amplified physiological information data. The AD convertor 45 is configured to execute AD conversion processing for the physiological information data output from the analog processor 43, based on a control signal output from the controller 40. That is, the AD convertor 45 is configured to convert the physiological information data, which is analog data, into digital data. Here, the AD conversion processing can include a series of processing including sampling processing, quantization processing and encoding processing.

Figure 4:
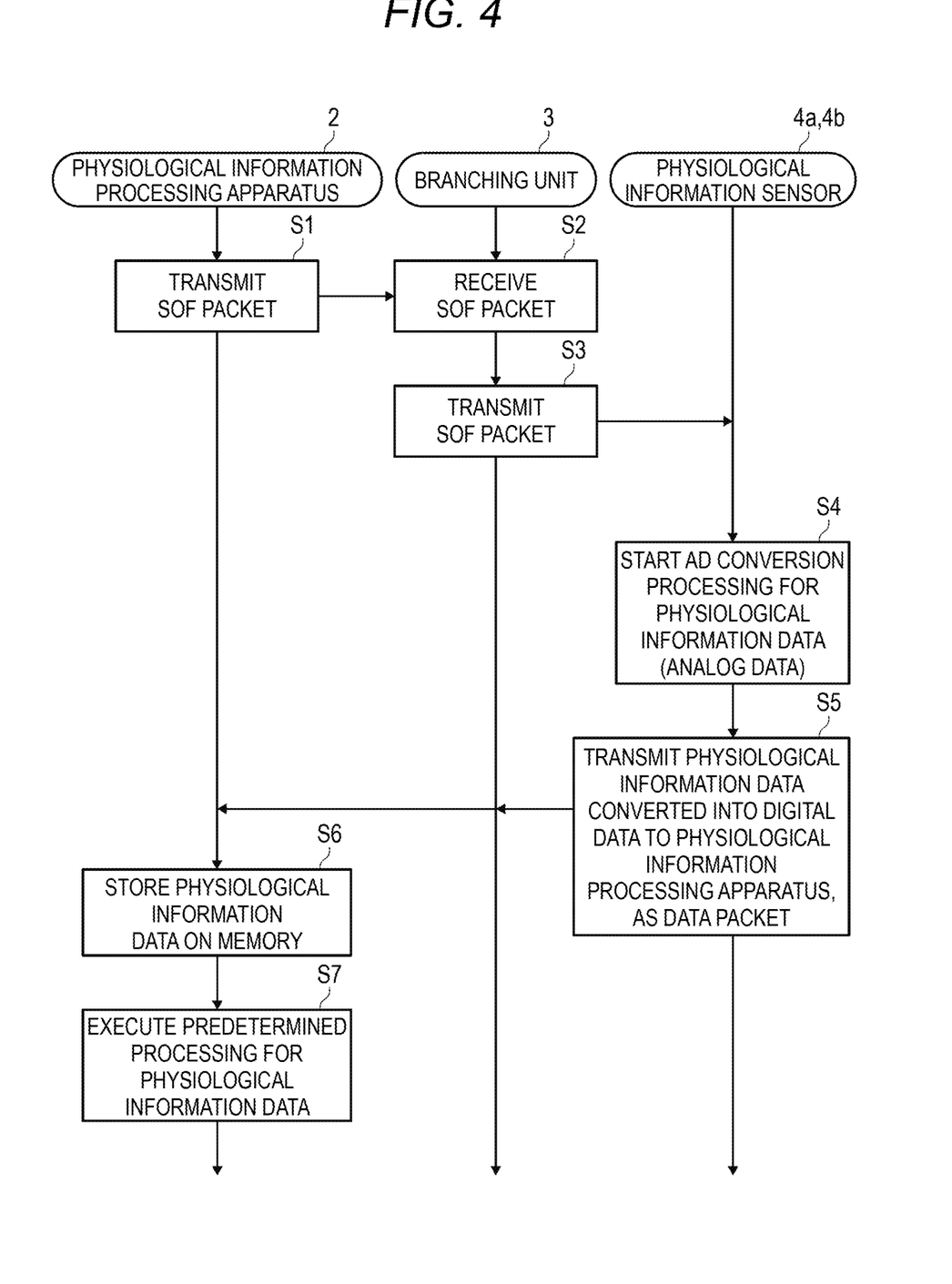
FIG. 4 is a flowchart for illustrating an example of a series of processing that is to be executed by the physiological information system.
Figure 5A:
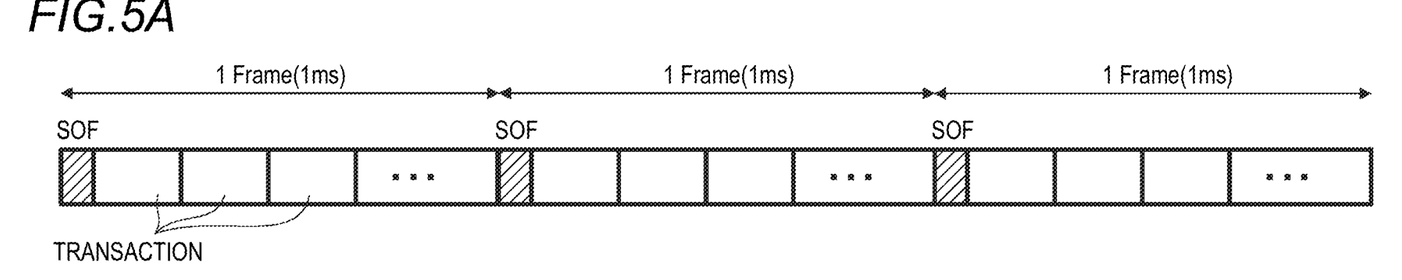
FIG. 5A illustrates an example of a configuration of a packet that is to be transferred between the physiological information processing apparatus and each physiological information sensor by USB communication.

Subsequently, the series of processing that is to be executed by the physiological information system 1 is described with reference to FIG. 4. FIG. 4 is a flowchart for illustrating an example of the series of processing that is to be executed by the physiological information system 1. As illustrated in FIG. 4, first, the controller 20 of the processing device 2 transmits an SOF (Start of Frame) packet (an example of a synchronous packet) to the branching unit 3 via the USB interface 24 (step S1). Here, as illustrated in FIG. 5A, in the USB communication protocol, data is transmitted and received in a frame unit. A time length of one frame may be, for example, 1 ms. Also, the time length of one frame is prescribed by a time interval between time at which the processing device 2 (host) transmits a predetermined SOF packet and time at which the processing device 2 transmits a next SOF packet of the predetermined SOF packet. For this reason, in a case in which the time length of one frame is 1 ms, the processing device 2 transmits the SOF packet toward each physiological information sensor 4 with a period of 1 ms.

Figure 5B:
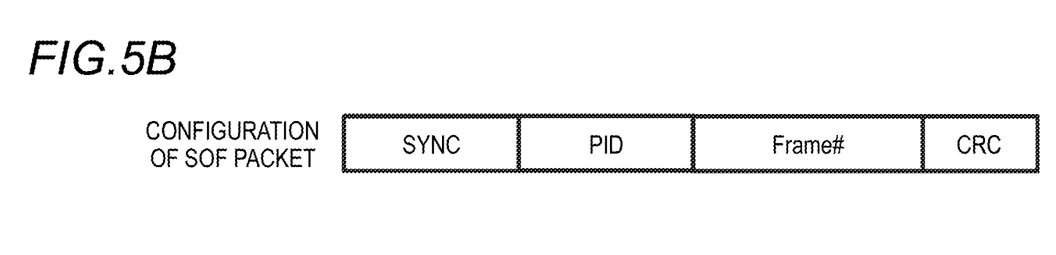
FIG. 5B illustrates an example of a configuration of an SOF packet.

Also, as illustrated in FIG. 5B, the SOF packet can include, for example, SYNC data (8 bits) for synchronization, PID data (8 bits) indicative of an identifier of the SOF packet, Frame number data (11 bits) indicative of a frame number of the SOF packet, and CRC data (5 bits) for check code. Here, the frame number indicates an order in which the SOF packet has been transmitted. Like this, the SOF packet can include information indicative of the frame number.

Figure 5C:
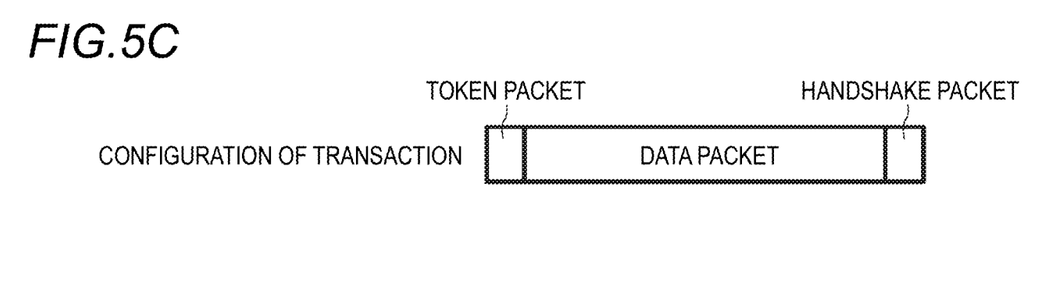
FIG. 5C illustrates an example of a configuration of transaction.

A plurality of transactions is transmitted and received in one frame. As illustrated in FIG. 5C, in one transaction, a token packet, a data packet, and a handshake packet are transmitted. For example, when the processing device 2 transmits a token packet indicative of the physiological information sensor 4a, as a device address, to the physiological information sensor 4a, the physiological information sensor 4a transmits a data packet, which includes the physiological information data converted into digital data, to the processing device 2. Then, the processing device 2 transmits a handshake packet to the physiological information sensor 4a as the physiological information data is received. In this way, in one transaction, the physiological information sensor 4a transmits the physiological information data to the processing device 2.

Then, the branching unit 3 (CPU) receives the SOF packet from the processing device 2 (step S2) and transmits the received SOF packet to the physiological information sensors 4a and 4b (step S3). In this respect, the branching unit 3 preferably transmits the SOF packet to the physiological information sensors 4a and 4b substantially at the same time.

Then, the physiological information sensor 4a starts the AD conversion processing (particularly, the sampling processing) for the physiological information data (analog data) acquired by the sensor unit 48 as the SOF packet is received (step S4). Specifically, the controller 40 of the physiological information sensor 4a controls the AD convertor 45 so that the AD convertor 45 starts the sampling processing of the physiological information data after predetermined time ΔT1 elapses from time at which the SOF packet is received. Thereafter, the physiological information sensor 4a (controller 40) transmits the physiological information data converted into the digital data and the data related to the frame number of the SOF packet to the processing device 2 via the branching unit 3, as the data packet (step S5).

Same or similarly, the physiological information sensor 4b starts the AD conversion processing (particularly, the sampling processing) for the physiological information data (analog data) acquired by the sensor unit 48 as the SOF packet is received (step S4). Specifically, the controller 40 of the physiological information sensor 4b controls the AD convertor 45 so that the AD convertor 45 starts the sampling processing of the physiological information data after predetermined time ΔT2 elapses from time at which the SOF packet is received. Thereafter, the physiological information sensor 4b (controller 40) transmits the physiological information data converted into the digital data and the data related to the frame number of the SOF packet to the processing device 2 via the branching unit 3, as the data packet (step S5). Here, the time at which the physiological information sensor 4a receives the SOF packet may be regarded as being substantially the same as the time at which the physiological information sensor 4b receives the SOF packet. Also, the predetermined time ΔT1 may be the same as the predetermined time ΔT2. In this case, it is possible to more accurately match the time at which the physiological information sensor 4a is to start the sampling processing for the physiological information data (hereinafter, referred to as 'physiological information data A') and the time at which the physiological information sensor 4b is to start the sampling processing for the physiological information data (hereinafter, referred to as 'physiological information data B').

Also, the transmission start time of the physiological information data B may be different from the transmission start time of the physiological information data A. In this respect, the physiological information sensor 4a may transmit the physiological information data A in a predetermined frame, and the physiological information sensor 4b may transmit the physiological information data B in a frame different from the predetermined frame.

Then, the processing device 2 receives the physiological information data A at time ta, and receives the physiological information data B at time tb (tb≠ta). Then, the processing device 2 stores the physiological information data A and the physiological information data B on the one or more memories. At this time, the processing device 2 can appropriately store the physiological information data transmitted as a data packet on the one or more memories by referring to the frame number of the SOF packet transmitted together with the physiological information data.

Then, the controller 20 of the processing device 2 executes predetermined processing for the physiological information data stored on the one or more memories (step S7). For example, the controller 20 may update the trend graph of the physiological information data displayed on the display unit 26. In this case, the controller 20 may update a trend graph of the physiological information data A and a trend graph of the physiological information data B. The trend graph of the physiological information data A and the trend graph of the physiological information data B may be displayed side by side on the same time axis. Alternatively, the controller 20 may execute first computation processing for the physiological information data A, and second computation processing for the physiological information data B. Also, the controller 20 may calculate a predetermined physiological information parameter, based on the physiological information data A and the physiological information data B. For example, when the physiological information data A indicates ECG data and the physiological information data B indicates pulse data, the controller 20 may calculate pulse wave transit time (PWTT), based on the ECG data and the pulse data.

In this way, the series of processing of the physiological information system 1 is executed. In the exemplary embodiment, whenever the processing device 2 transmits the SOF packet with a period of 1 ms, each physiological information sensor 4 executes the AD conversion processing for the physiological information data. However, the exemplary embodiment is not limited thereto. For example, when the processing device 2 transmits the SOF packet by a predetermined number of times (for example, two times or four times), each physiological information sensor 4 may execute one AD conversion processing.

According to the exemplary embodiment, each of the physiological information sensors 4a and 4b starts the AD conversion processing (particularly, the sampling processing) for the physiological information data (analog data) in accordance with the SOF packet transmitted from the processing device 2 via the branching unit 3. For this reason, the start time of the sampling processing for the physiological information data A, which is to be executed by the physiological information sensor 4a, and the start time of the sampling processing for the physiological information data B, which is to be executed by the physiological information sensor 4b, are substantially the same.

In this way, even when the respective physiological information sensors 4a and 4b transmit the physiological information data to the processing device 2 at different timings, the processing device 2 can execute the predetermined processing (for example, the update processing of the trend graph) for the physiological information data A and B (digital data) temporally synchronized. Also, since the processing device 2 can execute the predetermined processing for the physiological information data A and B temporally synchronized, it is possible to communicatively connect the processing device 2 and the physiological information sensors 4a and 4b by using the communication interface configured to transmit the digital data.

Therefore, it is possible to connect the plurality of physiological information sensors 4 to the processing device 2 by using the interface of the digital communication standard, and to increase a degree of layout (arrangement) freedom of each physiological information sensor. For this reason, it is possible to provide the physiological information system 1, the processing device 2 and the physiological information sensor 4 that have improved usability.

Also, according to the exemplary embodiment, since it is possible to interconnect each physiological information sensor 4 and the processing device 2 by using the digital communication cable, it is possible to increase the degree of layout freedom of each physiological information sensor 4. Also, each physiological information sensor 4 repeatedly executes the AD conversion processing for the physiological information data as the SOF packet transmitted with a predetermined period is received. In this way, the processing device 2 can acquire the physiological information data (digital data) from each physiological information sensor 4 in real time.

Meanwhile, in the exemplary embodiment, the physiological information data converted into the digital data and the data related to the frame number of the SOF packet are transmitted to the processing device 2, as the data packet. However, the exemplary embodiment is not limited thereto. For example, instead of the data related to the frame number, data related to the time interval between the transmission start time of the physiological information data and the start time of the AD conversion processing (specifically, the sampling processing) for the physiological information data and the physiological information data may be transmitted to the processing device 2, as the data packet. Also in this case, the processing device 2 can appropriately store the physiological information data transmitted as the data packet on the one or more memories by referring to the time interval between the transmission start time of the physiological information data and the start time of the AD conversion processing for the physiological information data.

Figure 6:
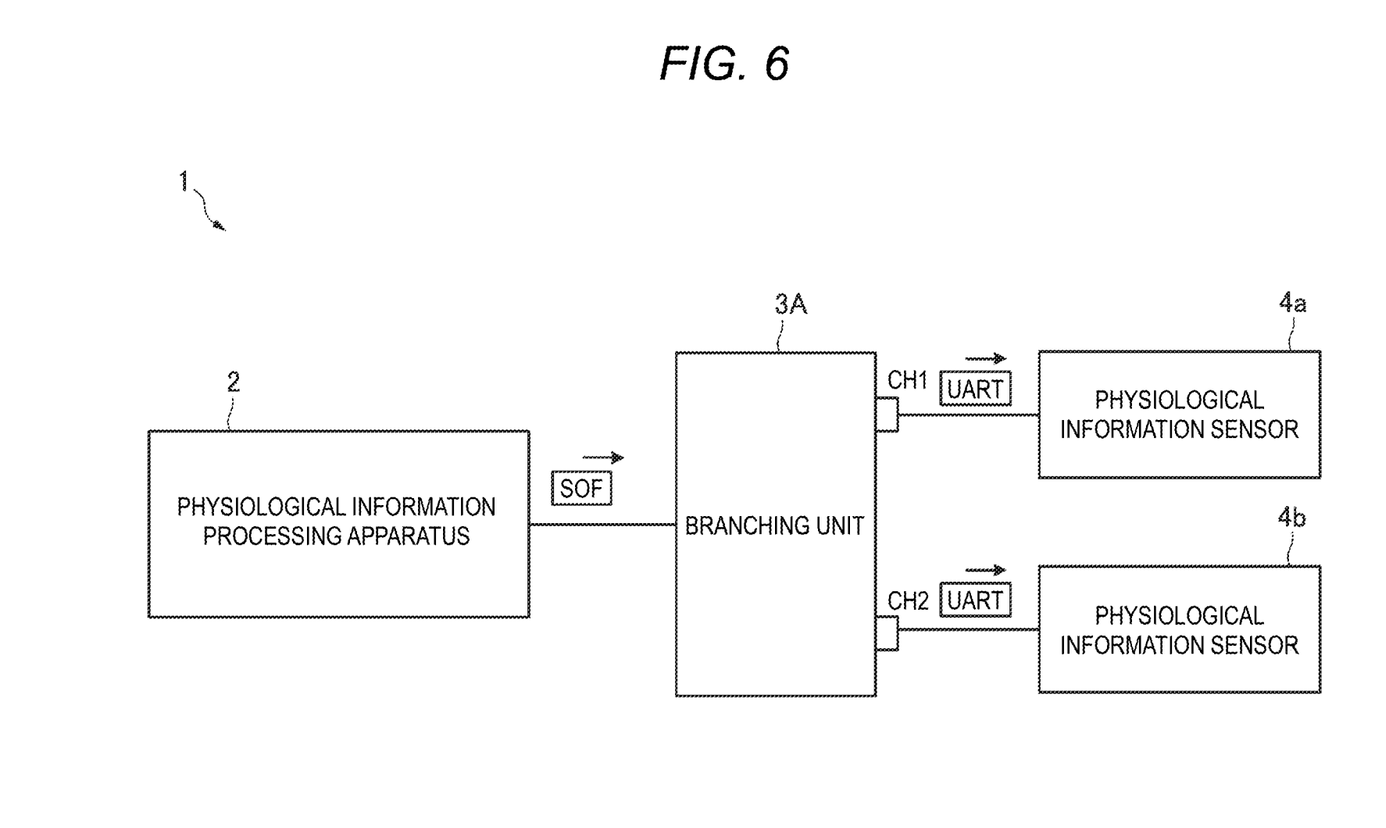
FIG. 6 illustrates an example of an entire configuration of a physiological information system in accordance with a modified embodiment.

Also, in the exemplary embodiment, the branching unit 3 transmits the SOF packet to each physiological information sensor 4. However, the exemplary embodiment is not limited thereto. For example, as illustrated in FIG. 6, in a physiological information system 1A of a modified embodiment, a branching unit 3A may be configured to generate a UART signal from the SOF packet received from the processing device 2 and to transmit the generated UART signal to each of the physiological information sensors 4a and 4b. The UART signal is an example of a trigger signal associated with the SOF packet. Also, the UART signal includes information related to the frame number of the transmitted SOF packet. In this case, each of the physiological information sensors 4a and 4b may be configured to start the AD conversion processing for the physiological information data as the UART signal is received. That is, each of the physiological information sensors 4a and 4b may be configured to start the sampling processing for the physiological information data after predetermined time elapses from time at which the UART signal is received. Thereafter, each of the physiological information sensors 4b and 4a is configured to transmit the physiological information data converted into the digital data and the data associated with the frame number of the SOF packet to the processing device 2 via the branching unit 3A, as the data packet.

Also, in the exemplary embodiment, the plurality of physiological information sensors 4 is connected to the processing device 2 by using the USB interface, which is a communication interface of the digital data. However, the exemplary embodiment is not limited thereto. For example, instead of the USB interface, an Ethernet (registered trademark) interface may be used. In this case, the branching unit 3 may be configured to generate the UART signal as a synchronous packet associated with an Ethernet communication protocol is received from the processing device 2, and to transmit the generated UART signal to each physiological information sensor 4. Then, each physiological information sensor 4 may be configured to start the AD conversion processing for the physiological information data as the UART signal is received. Also, after the branching unit 3 transmits the synchronous packet associated with the Ethernet communication protocol to each physiological information sensor 4, each physiological information sensor 4 may start the AD conversion processing for the physiological information data as the synchronous packet is received.

Also, in the exemplary embodiment, each physiological information sensor 4 executes the AD conversion processing for the physiological information data as the UART signal or the SOF packet is received. However, the exemplary embodiment is not limited thereto. For example, each physiological information sensor 4 may be configured to execute predetermined processing other than the AD conversion processing for the physiological information data as the UART signal or the SOF packet is received. Also, each physiological information sensor 4 may be configured to execute predetermined processing as the UART signal or the SOF packet is received. In this case, each physiological information sensor 4 may be configured to change a channel so as to input a correction signal or to execute the AD conversion processing for the correction signal.

Although the exemplary embodiment of the presently disclosed subject matter has been described, the technical scope of the presently disclosed subject matter should not be construed as being limited to the exemplary embodiment. The exemplary embodiment is merely exemplary, and diverse changes of the exemplary embodiment can be made within the scope of the claims by one skilled in the art. The technical scope of the presently disclosed subject matter should be determined by the scope of the claims and equivalents thereto.

What is claimed is:

1. A physiological information system comprising:
    a plurality of physiological information sensors configured to acquire physiological information data of a subject being tested, and
    a physiological information processing apparatus communicatively connected to each of the plurality of physiological information sensors,
    wherein the physiological information processing apparatus is configured to transmit a synchronous packet including frame identification information toward each of the plurality of physiological information sensors, and
    wherein each of the plurality of physiological information sensors is configured to:
        acquire respective physiological information data of the subject being tested;
        receive the synchronous packet transmitted from the physiological information processing apparatus or a trigger signal associated with the synchronous packet;
        start an AD conversion processing for the acquired respective physiological information data when receiving the synchronous packet or the trigger signal; and
        transmit the respective physiological information data converted into digital data and frame identification information corresponding to the digital data to the physiological information processing apparatus.

2. The physiological information system according to claim 1, wherein each of the plurality of physiological information sensors is communicatively connected to the physiological information processing apparatus via a digital communication cable.

3. The physiological information system according to claim 2, wherein the synchronous packet is an SOF (Start Of Frame) packet.

4. The physiological information system according to claim 1, wherein the physiological information processing apparatus is configured to transmit the synchronous packet toward each of the plurality of physiological information sensors with a predetermined period.

5. The physiological information system according to claim 1, wherein each of the plurality of physiological information sensors is configured to start the AD conversion processing for the respective physiological information data after predetermined time elapses from reception of the synchronous packet or the trigger signal.

6. The physiological information system according to claim 1, wherein each of the plurality of physiological information sensors is configured to transmit the respective physiological information data and data related to a time interval between a transmission start time of the physiological information data converted into the digital data and a start time of the AD conversion processing for the physiological information data to the physiological information processing apparatus.

7. The physiological information system according to claim 1, further comprising a branching unit connected to each of the plurality of physiological information sensors, wherein
the physiological information processing apparatus is communicatively connected to each of the plurality of physiological information sensors via the branching unit, and
the branching unit is configured to receive the synchronous packet from the physiological information processing apparatus and transmit the received synchronous packet to each of the plurality of physiological information sensors.

8. The physiological information system according to claim 1, wherein the physiological information apparatus is configured to:
receive, from each of the plurality of physiological information sensors, a plurality of the respective physiological information data converted into the digital data; and
display a plurality of trend graphs synchronized with each other, based on the plurality of received respective physiological information data converted into the digital data.

9. A physiological information sensor communicatively connected to a physiological information processing apparatus and configured to acquire physiological information data of a subject being tested,
wherein the physiological information sensor is configured to:
acquire the physiological information data of the subject being tested;
receive a synchronous packet that includes frame identification information and is transmitted from the physiological information processing apparatus or a trigger signal associated with the synchronous packet;
start AD conversion processing for the acquired physiological information data when receiving the synchronous packet or the trigger signal; and
transmit the physiological information data converted into digital data and frame identification information corresponding to the digital data to the physiological information processing apparatus.

10. A physiological information processing apparatus communicatively connected to a plurality of physiological information sensors configured to acquire physiological information data of a subject being tested,
wherein the physiological information processing apparatus is configured to:
transmit a synchronous packet including frame identification information to the plurality of physiological information sensors;
receive physiological information data, which has been converted into digital data through AD conversion processing, and frame identification information corresponding to the digital data from each of the plurality of physiological information sensors; and
execute predetermined processing for the received physiological information data,
the AD conversion processing is started when the synchronous packet transmitted from the physiological information processing apparatus or a trigger signal associated with the synchronous packet is received.

11. A physiological information system comprising:
a plurality of physiological information sensors configured to acquire physiological information data of a subject being tested; and
a physiological information processing apparatus communicatively connected to each of the plurality of physiological information sensors,
wherein the physiological information processing apparatus is configured to transmit a synchronous packet including frame identification information toward each of the plurality of physiological information sensors, and
wherein each of the plurality of physiological information sensors is configured to:
acquire respective physiological information data of the subject being tested;
receive the synchronous packet transmitted from the physiological information processing apparatus or a trigger signal associated with the synchronous packet;
start predetermined processing when receiving the synchronous packet or the trigger signal; and
transmit the respective physiological information data converted into digital data and frame identification information corresponding to the digital data to the physiological information processing apparatus.

12. A physiological information system comprising:
a plurality of physiological information sensors configured to acquire physiological information data of a subject being tested, and
a physiological information processing apparatus communicatively connected to each of the plurality of physiological information sensors,
wherein the physiological information processing apparatus is configured to transmit a synchronous packet including frame identification information toward each of the plurality of physiological information sensors, and
wherein each of the plurality of physiological information sensors is configured to:
acquire respective physiological information data of the subject being tested;

receive, substantially at a same time as the other plurality of physiological information sensors, the synchronous packet transmitted from the physiological information processing apparatus or a trigger signal associated with the synchronous packet;

start an AD conversion processing for the acquired respective physiological information data when receiving the synchronous packet or the trigger signal; and transmit the respective physiological information data converted into digital data and frame identification information corresponding to the digital data to the physiological information processing apparatus.

13. A physiological information sensor communicatively connected to a physiological information processing apparatus and configured to acquire physiological information data of a subject being tested, wherein the physiological information sensor is configured to:

acquire the physiological information data of the subject being tested;

receive, substantially at a same time as other physiological information sensors, a synchronous packet that includes frame identification information and is transmitted from the physiological information processing apparatus or a trigger signal associated with the synchronous packet;

start an AD conversion processing for the acquired physiological information data when receiving the synchronous packet or the trigger signal; and transmit the physiological information data converted into digital data and frame identification information corresponding to the digital data to the physiological information processing apparatus.

14. A physiological information processing apparatus communicatively connected to a plurality of physiological information sensors configured to acquire physiological information data of a subject being tested, wherein the physiological information processing apparatus is configured to:

transmit a synchronous packet including frame identification information to the plurality of physiological information sensors substantially at a same time;

receive physiological information data, which has been converted into digital data through an AD conversion processing, and frame identification information corresponding to the digital data from each of the plurality of physiological information sensors; and execute predetermined processing for the received physiological information data, wherein the AD conversion processing is started when the synchronous packet transmitted from the physiological information processing apparatus or a trigger signal associated with the synchronous packet is received.

15. A physiological information system comprising:

a plurality of physiological information sensors configured to acquire physiological information data of a subject being tested; and a physiological information processing apparatus communicatively connected to each of the plurality of physiological information sensors, wherein the physiological information processing apparatus is configured to transmit a synchronous packet including frame identification information toward each of the plurality of physiological information sensors, and wherein each of the plurality of physiological information sensors is configured to:

acquire respective physiological information data of the subject being tested;

receive, substantially at a same time as the other physiological information sensors, the synchronous packet transmitted from the respective physiological information processing apparatus or a trigger signal associated with the synchronous packet;

start predetermined processing when receiving the synchronous packet or the trigger signal; and transmit the respective physiological information data converted into digital data and frame identification information corresponding to the digital data to the physiological information processing apparatus.

* * * * *